US007290545B2

(12) United States Patent
Kleman et al.

(10) Patent No.: US 7,290,545 B2
(45) Date of Patent: Nov. 6, 2007

(54) FACE MASK WITH ANTI-FOG FOLDING

(75) Inventors: Angela M. Kleman, Toledo, OH (US); Eric C. Steindorf, Roswell, GA (US); Tameka Spence, Lawrenceville, GA (US); Kiran K. Reddy, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 150 days.

(21) Appl. No.: 11/021,543

(22) Filed: Dec. 23, 2004

(65) Prior Publication Data

US 2006/0137691 A1 Jun. 29, 2006

(51) Int. Cl.
*A61F 11/00* (2006.01)

(52) U.S. Cl. .......................... 128/206.19; 128/206.12; 128/206.13

(58) Field of Classification Search ........... 128/205.25, 128/205.29, 206.12, 206.13, 206.16, 206.19, 128/206.21
See application file for complete search history.

(56) References Cited

U.S. PATENT DOCUMENTS 3,338,992 A 8/1967 Kinney
3,341,394 A 9/1967 Kinney
3,502,763 A 3/1970 Hartmann
3,542,615 A 11/1970 Dobo et al.
3,692,618 A 9/1972 Dorschner et al.
3,802,817 A 4/1974 Matsuki et al.
3,849,241 A 11/1974 Butin et al.
3,953,566 A 4/1976 Gore
4,100,324 A 7/1978 Anderson et al.
4,187,390 A 2/1980 Gore
4,215,682 A 8/1980 Kubik et al.
4,259,748 A 4/1981 Miller
4,340,563 A 7/1982 Appel et al.
4,374,888 A 2/1983 Bornslaeger
4,375,718 A 3/1983 Wadsworth et al.
4,443,513 A 4/1984 Meitner et al.
4,592,815 A 6/1986 Nakao
4,631,933 A 12/1986 Carey, Jr.
4,652,487 A 3/1987 Morman
4,655,760 A 4/1987 Morman et al.
4,657,802 A 4/1987 Morman
4,720,415 A 1/1988 Vander Wielen et al.
4,781,966 A 11/1988 Taylor
4,789,699 A 12/1988 Kieffer et al.

(Continued)

OTHER PUBLICATIONS

U.S. Appl. No. 10/970,457, filed Oct. 21, 2004.

(Continued)

*Primary Examiner*—Steven O. Douglas
(74) *Attorney, Agent, or Firm*—Dority & Manning

(57) ABSTRACT

A face mask is provided that is configured to reduce or eliminate fogging that may occur on eye wear or an eye-shield worn by a user of the face mask. The face mask includes a body portion that has a layer with an inner surface configured for facing the face of the user. The layer has at least one fold that extends in a horizontal direction across at least a portion of the layer. The fold has a fold forming portion located between and attached to two primary portions of the layer. The inner surface of the fold forming portion is in facing relationship with the inner surface of the vertically disposed lower primary portion.

20 Claims, 5 Drawing Sheets

U.S. PATENT DOCUMENTS

| | | | | |
|---|---|---|---|---|
| 4,802,473 | A | | 2/1989 | Hubbard et al. |
| 4,818,464 | A | | 4/1989 | Lau |
| 4,874,659 | A | | 10/1989 | Ando et al. |
| 4,891,957 | A | | 1/1990 | Strack et al. |
| 4,965,122 | A | | 10/1990 | Morman |
| 4,969,457 | A | | 11/1990 | Hubbard et al. |
| 4,981,747 | A | | 1/1991 | Morman |
| 5,020,533 | A | | 6/1991 | Hubbard et al. |
| 5,114,781 | A | | 5/1992 | Morman |
| 5,226,992 | A | | 7/1993 | Morman |
| 5,244,482 | A | | 9/1993 | Hassenboehler, Jr. et al. |
| 5,322,061 | A | | 6/1994 | Brunson |
| 5,336,545 | A | | 8/1994 | Morman |
| 5,383,450 | A | | 1/1995 | Hubbard et al. |
| 5,401,466 | A | | 3/1995 | Foltz et al. |
| 5,492,753 | A | | 2/1996 | Levy et al. |
| 5,493,753 | A | | 2/1996 | Rostamo |
| 5,540,976 | A | | 7/1996 | Shawver et al. |
| 5,553,608 | A | | 9/1996 | Reese et al. |
| 5,681,645 | A | | 10/1997 | Strack et al. |
| 5,699,791 | A | | 12/1997 | Sukiennik et al. |
| 5,813,398 | A | | 9/1998 | Baird et al. |
| 5,927,280 | A | * | 7/1999 | Miyake ...................... 128/857 |
| 6,062,220 | A | | 5/2000 | Whitaker et al. |
| 6,213,125 | B1 | * | 4/2001 | Reese et al. ................ 128/857 |
| 6,412,486 | B1 | | 7/2002 | Glass |
| 6,474,336 | B1 | | 11/2002 | Wolfe |
| 6,484,722 | B2 | | 11/2002 | Bostock et al. |
| 6,520,181 | B2 | | 2/2003 | Baumann et al. |
| 6,644,314 | B1 | | 11/2003 | Elsberg |
| 2004/0078869 | A1 | | 4/2004 | Bell et al. |
| 2004/0121107 | A1 | | 6/2004 | Bell et al. |

OTHER PUBLICATIONS

U.S. Appl. No. 10/743,260, filed Dec. 22, 2003.
U.S. Appl. No. 11/020,738, filed Dec. 22, 2004.
U.S. Appl. No. 11/022,379, filed Dec. 21, 2004.
U.S. Appl. No. 11/020,734, filed Dec. 22, 2004.

* cited by examiner

FACE MASK WITH ANTI-FOG FOLDING

BACKGROUND

Face masks find utility in a variety of medical, industrial and household applications by protecting the wearer from inhaling dust and other harmful airborne contaminates through their mouth or nose. The use of face masks is a recommended practice in the healthcare industry to help prevent the spread of disease. Face masks worn by health-care providers help reduce infections in patients by filtering the air exhaled from the wearer thus reducing the number of harmful organisms or other contaminants released into the environment. Additionally, face masks protect the healthcare worker by filtering airborne contaminants and microorganisms from the inhaled air.

The section of the face mask that covers the nose and mouth is typically known as the body portion. The body portion of the mask may be comprised of several layers of material. At least one layer is composed of a filtration material that prevents the passage of germs and other contaminants therethrough but allows for the passage of air so that the user may comfortably breathe. The porosity of the mask refers to how easily air is drawn through the mask. A more porous mask is easier to breathe through. The body portion may also contain multiple layers to provide additional functionality or attributes to the face mask. For example, many face masks include one or more layers of material on either side of the filtration media layer. Further components may be attached to the mask to provide additional functionality. A clear plastic face shield intended to protect the user's face from splashed fluid is one example.

When using a properly donned face mask, the heat and moisture of the user's exhaled breath tends to concentrate inside. As this humidified air escapes the face mask, it can condense on the user's eye wear or face shield causing fogging which may hamper the sight of the healthcare worker.

The body portion of face masks are typically provided with one or more folds that extend in the horizontal direction across the length of the body portion. The folds allow the face mask to be adjusted vertically or otherwise so as to allow the face mask to conform to the face of the user and create a breathing chamber for the respirated air. The folds on the inner surface of the face mask are folded down and towards the face and eyes of the user. This folding arrangement may be problematic in that moisture in airflow in the face mask may be directed upwards towards the eye wear or face shield of the user resulting in fogging.

A prior face mask 10 is shown in FIGS. 1 and 2. The face mask 10 includes a body portion 12 made of at least one layer 16 of material that includes a series of folds 20 so as to allow for the aforementioned adjustment of the face mask 10. Layer 16 includes an inner surface 18 that generally faces towards the face of a user when the face mask 10 is worn. The layer 16 is made of a plurality of primary portions 32, 34, 36 and 38 that are spaced from one another by a series of fold forming portions 26, 28 and 30. The face mask 10 in FIGS. 1 and 2 is arranged so as to have the inner surface 18 of the fold forming portion 26 be in opposing relationship to the inner surface 18 of the primary portion 32 that is vertically disposed below the fold forming portion 26. Likewise, the inner surface 18 of the fold forming portion 28 is in opposing relationship to the inner surface 18 of the primary portion 34 that is disposed vertically below the fold forming portion 28. Still further, the inner surface 18 of the fold forming portion 30 is in opposing relationship to the inner surface 18 of the primary portion 36 that is vertically disposed below the fold forming portion 30. The inner surface 18 of the fold forming portions 26, 28 and 30 are in facing relationship with the primary portions 34, 36 and 38 that are vertically disposed above each of the respected fold forming portions 26, 28 and 30. The orientation of the folds 20 in layer 16 is problematic in that moisture in air flow in the face mask 10 is directed upwards towards the eye wear or face shield of the user of the face mask 10 thus resulting in fogging of their surfaces.

SUMMARY

Various features and advantages of the invention will be set forth in part in the following description, or may be obvious from the description, or may be learned from practice of the invention.

A face mask that includes a body portion with a layer that has an inner surface configured for facing the face of a user is provided in one exemplary embodiment. The layer has at least one fold that extends in a horizontal direction across at least a portion of the layer. The fold has a fold forming portion located between and attached to two primary portions of the layer. The inner surface of the fold forming portion is in facing relationship with the inner surface of the vertically disposed lower primary portion. The fold configuration of the face mask redirects air flow within so as to reduce or eliminate fogging that may occur on eye wear or a face shield worn by a user.

In accordance with another exemplary embodiment, a face mask is provided with a body portion configured to be placed over a mouth and at least part of a nose of a user in order to isolate the mouth and the at least part of the nose of the user from the environment so that the respiration air is drawn through the body portion. The body portion has a layer with an inner surface that has a part configured for contacting the face of the user. The layer has a plurality of folds that extend across the entire horizontal length of the layer. Each of the folds have a fold forming portion located between and attached to two primary portions of the layer. The inner surface of the fold forming portion is in facing relationship with the inner surface of the vertically disposed lower primary portion. Likewise, the inner surface of the fold forming portion is in opposing relationship with the inner surface of the vertically disposed upper primary portion. An anti-fog strip is located on a top edge of the body portion.

An exemplary embodiment of the face mask as discussed above also exists where the body portion has a second layer with an outer surface at least a part of which may be configured for facing the environment. The second layer has a plurality of folds that extend across the entire horizontal length of the second layer. Each of the folds in the second layer has a fold forming portion located between and attached to two primary portions of the second layer. The outer surface of the fold forming portion of the second layer is in facing relationship with the outer surface of the vertically disposed lower primary portion of the second layer. Likewise, the outer surface of the fold forming portion of the second layer is in opposing relationship with the outer surface of the vertically disposed upper primary portion of the second layer.

Also provided for in accordance with an exemplary embodiment is a face mask as discussed above where the body portion has a third layer disposed between the layer with the inner surface and the second layer. Further, in accordance with another exemplary embodiment, the layer with the inner surface is made of a wet laid material while the second layer may be made of a spunbond material. The third layer may be made of a meltblown material.

Also provided for in accordance with another exemplary embodiment is a face mask as described above where the body portion has binding on a pair of horizontal ends of the body portion so as to limit unfolding of the fold or folds.

Another exemplary embodiment exists where the fold or folds are configured to be at least partially unfolded so as to shape the body portion so that the inner surface at least partially defines a chamber when the body portion is placed over the mouth and at least part of the nose of the user.

Also provided is a face mask in accordance with another exemplary embodiment that includes a body portion that is configured to be placed over a mouth and at least part of a nose of a user in order to isolate the mouth and at least part of the nose of the user from the environment so that respiration air is drawn through the body portion. The body portion may have a layer with an inner surface a part of which is configured for contacting the face of the user. The layer has a plurality of folds that extend across the entire horizontal length of the layer. Each of the folds has a fold forming portion located between and attached to two primary portions of the layer. The inner surface of the fold forming portion is in facing relationship with the inner surface of the vertically disposed lower primary portion. The inner surface of the fold forming portion is in opposing relationship with the inner surface of the vertically disposed upper primary portion. The body portion has a second layer with an outer surface at least a part of which is configured for facing the environment. The second layer also has a plurality of folds that extend across the entire horizontal length of the second layer. Each of the folds of the second layer have a fold forming portion located between and attached to two primary portions of the second layer. The outer surface of the fold forming portion of the second layer is in facing relationship with the outer surface of the vertically disposed lower primary portion of the second layer. Likewise, the outer surface of the fold forming portion of the second layer is in opposing relationship with the outer surface of the vertically disposed upper primary portion of the second layer. The body portion has a third layer disposed between the layer with the inner surface and the second layer. The body portion also has binding on a pair of horizontal ends of the body portion so as to limit unfolding of the plurality of folds in the layer with the inner surface and the second layer. Further, a fastening member is attached to the body portion and configured so as to retain the body portion onto the face of the user.

These and other features, aspects and advantages of the present invention will become better understood with reference to the following description and appended claims. The accompanying drawings, which are incorporated in and constitute part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
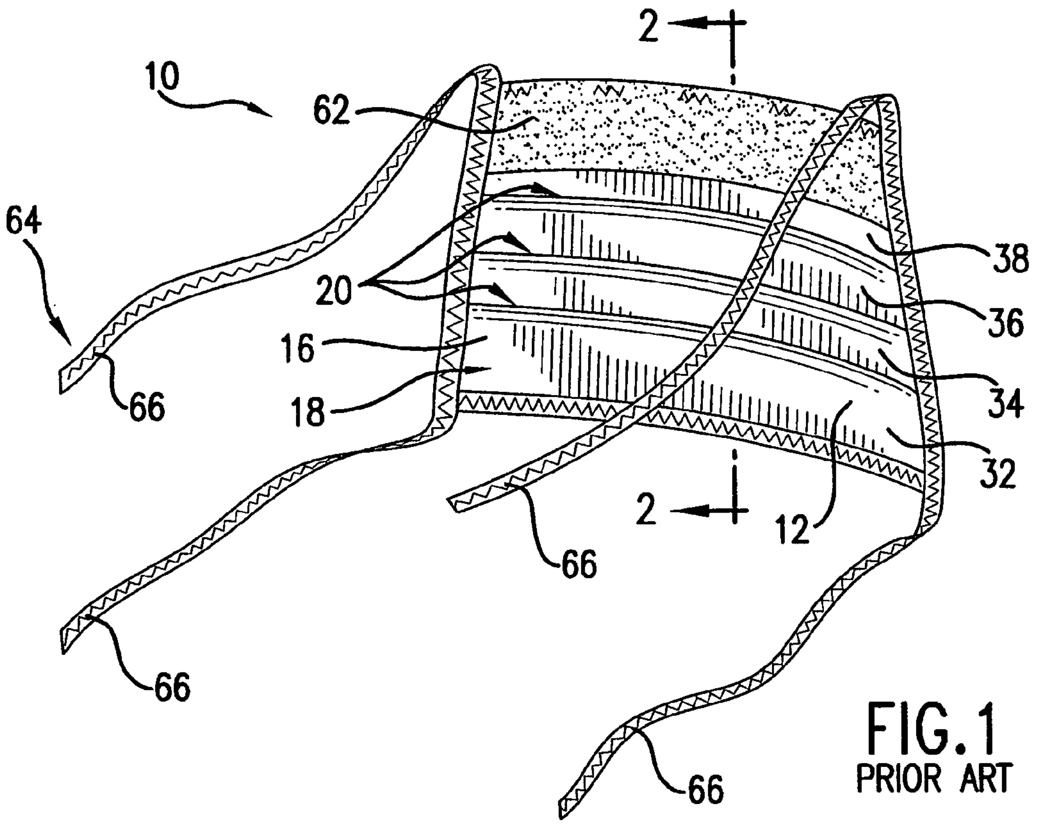
FIG.1 PRIOR ART
FIG. 1 is a perspective view of a prior face mask with a body portion that is folded.

Repeat use of reference characters in the present specification and drawings is intended to present same or analogous features or elements of the invention.

DEFINITIONS

As used herein, the term "nonwoven fabric or web" means a web having a structure of individual fibers or threads which are interlaid, but not in an identifiable manner as in a knitted fabric. Nonwoven fabrics or webs have been formed from various processes such as, for example, meltblowing processes, spunbonding processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91).

As used herein, the term "ultrasonic bonding" refers to a process in which materials (fibers, webs, films, etc.) are joined by passing the materials between a sonic horn and anvil roll. An example of such a process is illustrated in U.S. Pat. No. 4,374,888 to Bornslaeger, the entire contents of which are incorporated herein by reference in their entirety for all purposes.

As used herein, the term "thermal point bonding" involves passing materials (fibers, webs, films, etc.) to be bonded between a heated calender roll and a heated anvil roll. The calender roll is usually, though not always, engraved with a pattern in some way such that the entire fabric is not bonded across its entire surface. The surface of the anvil roll is usually flat and/or smooth. As a result, various patterns for calender rolls have been developed for functional as well as aesthetic reasons. Typically, the percent bonding area varies from around 10 percent to around 30 percent of the area of the fabric laminate. The bonded areas are typically discrete points or shapes and not interconnected. As is well known in the art, thermal point bonding holds the laminate layers together and imparts integrity and strength to the nonwoven material by bonding filaments and/or fibers together thereby limiting their movement.

As used herein, the term "electret" or "electret treating" refers to a treatment that imparts a charge to a dielectric material, such as a polyolefin. The charge includes layers of positive or negative charges trapped at or near the surface of the polymer, or charge clouds stored in the bulk of the polymer. The charge also includes polarization charges which are frozen in alignment of the dipoles of the molecules. Methods of subjecting a material to electret treating are well known by those skilled in the art. These methods include, for example, thermal, liquid-contact, electron beam, and corona discharge methods. One particular technique of subjecting a material to electret treating is disclosed in U.S. Pat. No. 5,401,466, the entire contents of which are incorporated herein by reference in their entirety for all purposes. This technique involves subjecting a material to a pair of electrical fields wherein the electrical fields have opposite polarities.

As used herein, the term "spunbonded fibers" refers to small diameter fibers which are formed by extruding molten thermoplastic material as filaments from a plurality of fine, usually circular capillaries of a spinneret with the diameter of the extruded filaments then being rapidly reduced to fibers as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al., the entire contents of which are incorporated herein by reference in their entirety for all purposes. Spunbond fibers are generally continuous and have diameters generally greater than about 7 microns, more particularly, between about 10 and about 40 microns.

As used herein, the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al., the entire contents of which are incorporated herein by reference in their entirety for all purposes. Meltblown fibers are microfibers which may be continuous or discontinuous with diameters generally less than 10 microns.

As used herein, the term "stretch bonded laminate" refers to a composite material having at least two layers in which one layer is a gatherable layer and the other layer is an elastic layer. The layers are joined together when the elastic layer is extended from its original condition so that upon relaxing the layers, the gatherable layer is gathered. Such a multilayer composite elastic material may be stretched to the extent that the nonelastic material gathered between the bond locations allows the elastic material to elongate. One type of stretch bonded laminate is disclosed, for example, by U.S. Pat. No. 4,720,415 to Vander Wielen et al., the entire contents of which are incorporated herein by reference in their entirety for all purposes. Other composite elastic materials are disclosed in U.S. Pat. No. 4,789,699 to Kieffer et al., U.S. Pat. No. 4,781,966 to Taylor and U.S. Pat. Nos. 4,657,802 and 4,652,487 to Morman and U.S. Pat. No. 4,655,760 to Morman et al., the entire contents of which are incorporated herein by reference in their entirety for all purposes.

As used herein, the terms "necking" or "neck stretching" interchangeably refer to a method of elongating a nonwoven fabric, generally in the machine direction, to reduce its width (cross-machine direction) in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.6 times. When relaxed, the web retracts toward, but does not return to, its original dimensions. Such a process is disclosed, for example, in U.S. Pat. No. 4,443,513 to Meitner and Notheis, U.S. Pat. Nos. 4,965,122, 4,981,747 and 5,114,781 to Morman and U.S. Pat. No. 5,244,482 to Hassenboehler Jr. et al., the entire contents of which are incorporated herein by reference in their entirety for all purposes.

As used herein, the term "necked material" refers to any material which has undergone a necking or neck stretching process.

As used herein, the term "reversibly necked material" refers to a material that possesses stretch and recovery characteristics formed by necking a material, then heating the necked material, and cooling the material. Such a process is disclosed in U.S. Pat. No. 4,965,122 to Mormbn, the entire contents of which are incorporated by reference herein in their entirety for all purposes.

As used herein, the term "neck bonded laminate" refers to a composite material having at least two layers in which one layer is a necked, non-elastic layer and the other layer is an elastic layer. The layers are joined together when the non-elastic layer is in an extended (necked) condition. Examples of neck-bonded laminates are such as those described in U.S. Pat. Nos. 5,226,992, 4,981,747, 4,965,122 and 5,336,545 to Morman, the entire contents of which are incorporated herein by reference in their entirety for all purposes.

As used herein, the term "coform" means a meltblown material to which at least one other material is added during the meltblown material formation. The meltblown material may be made of various polymers, including elastomeric polymers. Various additional materials may be added to the meltblown fibers during formation, including, for example, pulp, superabsorbent particles, cellulose or staple fibers. Coform processes are illustrated in commonly assigned U.S. Pat. No. 4,818,464 to Lau and U.S. Pat. No. 4,100,324 to Anderson et al., the entire contents of which are incorporated herein by reference in their entirety for all purposes.

As used herein, the term "elastic" refers to any material, including a film, fiber, nonwoven web, or combination thereof, which upon application of a biasing force, is stretchable to a stretched, biased length which is at least about 150 percent, or one and a half times, its relaxed, unstretched length, and which will recover at least 15 percent of its elongation upon release of the stretching, biasing force.

As used herein, the term "extensible and retractable" refers to the ability of a material to extend upon stretch and retract upon release. Extensible and retractable materials are those which, upon application of a biasing force, are stretchable to a stretched, biased length and which will recover a portion, preferably at least about 15 percent, of their elongation upon release of the stretching, biasing force.

As used herein, the terms "elastomer" or "elastomeric" refer to polymeric materials that have properties of stretchability and recovery.

As used herein, the terms "stretch" or "stretched" refers to the ability of a material to extend upon application of a biasing force. Percent stretch is the difference between the initial dimension of a material and that same dimension after the material has been stretched or extended following the application of a biasing force. Percent stretch may be expressed as [(stretched length B initial sample length)/initial sample length]×100. For example, if a material having an initial length of one (1) inch is stretched 0.50 inch, that is, to an extended length of 1.50 inches, the material can be said to have a stretch of 50 percent.

As used herein, the term "recover" or "recovery" refers to a contraction of a stretched material upon termination of a biasing force following stretching of the material by application of the biasing force. For example, if a material having a relaxed, unbiased length of one (1) inch is elongated 50 percent by stretching to a length of one and one half (1.5) inches the material would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its elongation.

As used herein, the term "composite" refers to a material which may be a multicomponent material or a multilayer material. These materials may include, for example, spunbond-meltblown-spunbond, stretch bonded laminates, neck bonded laminates, or any combination thereof.

As used herein, the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

These terms may be defined With additional language in the remaining portions of the specification.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges and limits mentioned herein include all ranges located within, and also all values located under or above the prescribed limits. It is to be also understood that all ranges mentioned herein include all subranges included in the mentioned ranges. For instance, a range from 100-200 also includes ranges from 110-150, 170-190, and 153-162. Further, all limits mentioned herein include all other limits included in the mentioned limits. For instance, a limit of up to about 7 also includes a limit of up to about 5, up to about 3, and up to about 4.5.

Various exemplary embodiments provide for a face mask 10 that has a body portion 12 made of at least one layer 16 with an inner surface 18. The layer 16 includes at least one fold 20 that allows for adjustment of the size and/or shape of the body portion 12. The fold 20 is configured in a manner that redirects the air flow within face mask 10 when worn so as to be downward and/or away from eye wear or a face shield that may be worn by a user 14 so as to reduce the likelihood of fogging of the eye wear or the eyeshield.

Figure 3:
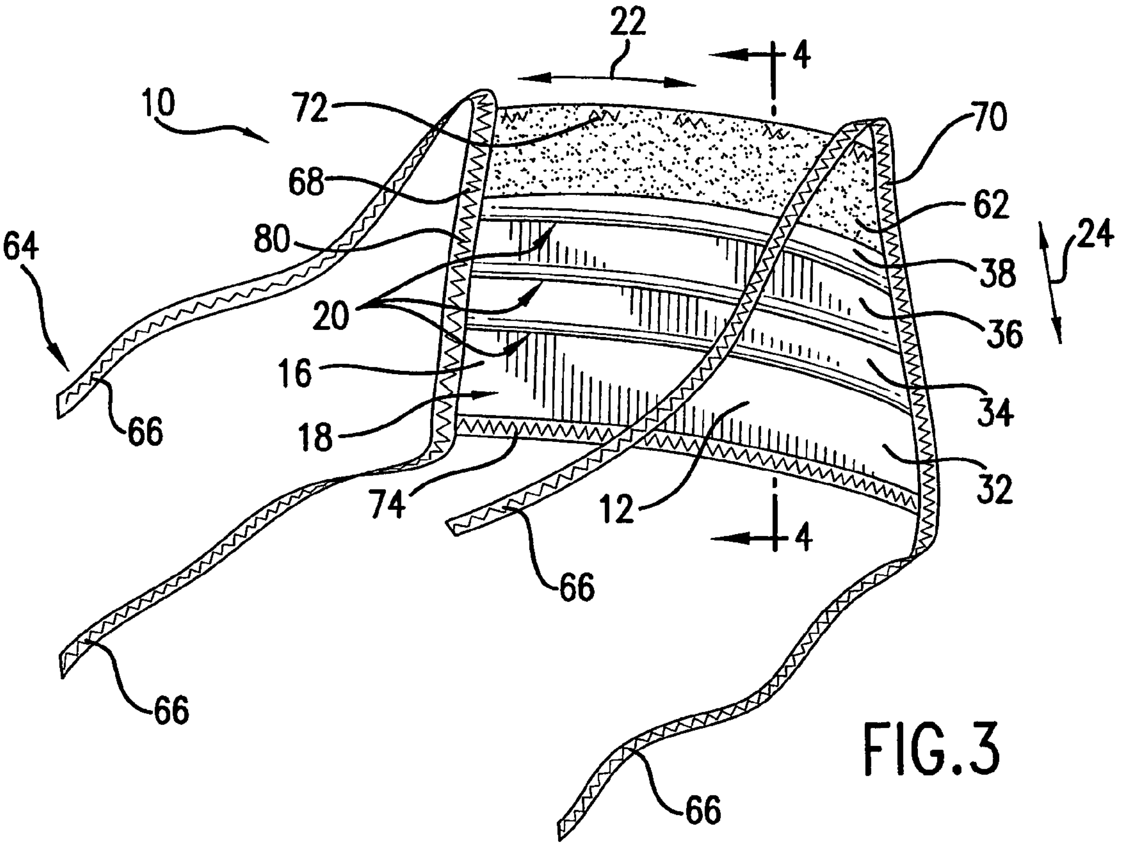
FIG. 3 is a perspective view of an exemplary embodiment of a face mask that has a body portion that is folded.
Figure 4:
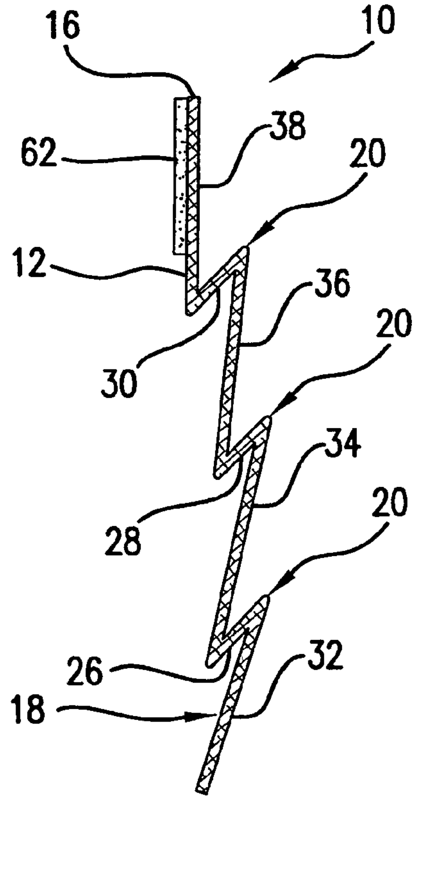
FIG. 4 is a cross-sectional view along line 4-4 in FIG. 3.

FIGS. 3 and 4 show an exemplary embodiment of a face mask 10. The body portion 12 of the face mask 10 is shown as being made from a single layer 16 that has three folds 20 that extend along the horizontal length 22 of the layer 16. The folds 20 can be unfolded so as to increase the size of the body portion 12 or to otherwise adjust the shape of the body portion 12 as desired. The folds 20 are formed from a plurality of fold forming portions 26, 28 and 30 that are intermittent a plurality of primary portions 32, 34, 36 and 38 of the layer 16. The inner surface 18 of the fold forming portion 26 is in facing relationship with the inner surface 18 of the primary portion 32 that is disposed lower vertically from the fold forming portion 26. The inner surface 18 of the fold forming portion 26 is in opposing relationship to the inner surface 18 of the primary portion 34 that is disposed vertically above the fold forming portion 26.

Figure 2:
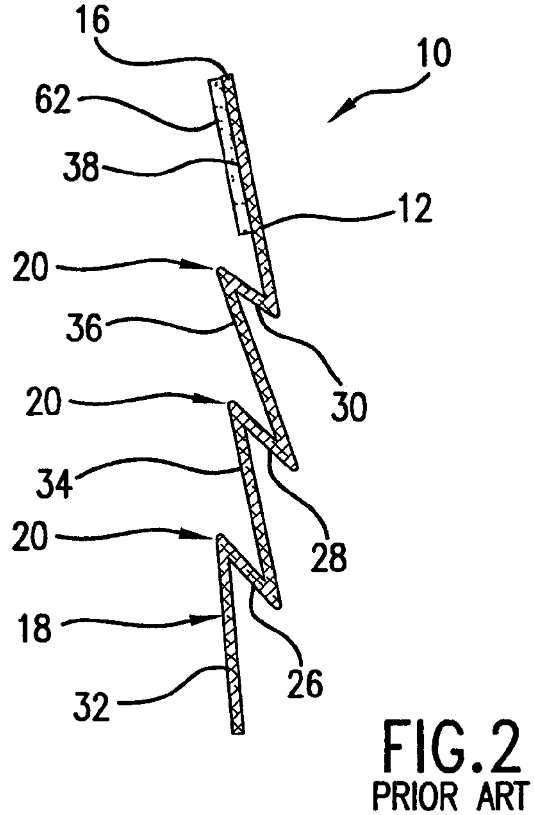
FIG.2 PRIOR ART
FIG. 2 is a cross-sectional view along line 2-2 in FIG. 1.

Arrangement of the other fold forming portions 28 and 30 in the layer 16 is made in a manner similar to that of the fold forming portion 26. For example, the inner surface 18 of the fold forming portion 28 is in facing relationship with the inner surface 18 of the vertically disposed lower primary portion 34 while the inner surface 18 of the fold forming portion 28 is in opposing relationship with the inner surface 18 of the vertically disposed upper primary portion 36. In a similar fashion, the inner surface 18 of the fold forming portion 30 is in facing relationship with the inner surface 18 of the vertically disposed lower primary portion 36 while the inner surface 18 of the fold forming portion 30 is in opposing relationship with the inner surface 18 of the vertically disposed upper primary portion 38. While the exemplary embodiment shown in FIGS. 3 and 4 employ three folds 20 that are arranged in a similar fashion, it is to be understood that in accordance with other exemplary embodiments that only one of the folds 20 may be arranged as discussed. For example, in accordance with another exemplary embodiment only one of the folds 20 is arranged as discussed while other folds 20 in the layer 16 are arranged as that shown in the prior face mask 10 of FIGS. 1 and 2.

Figure 5:
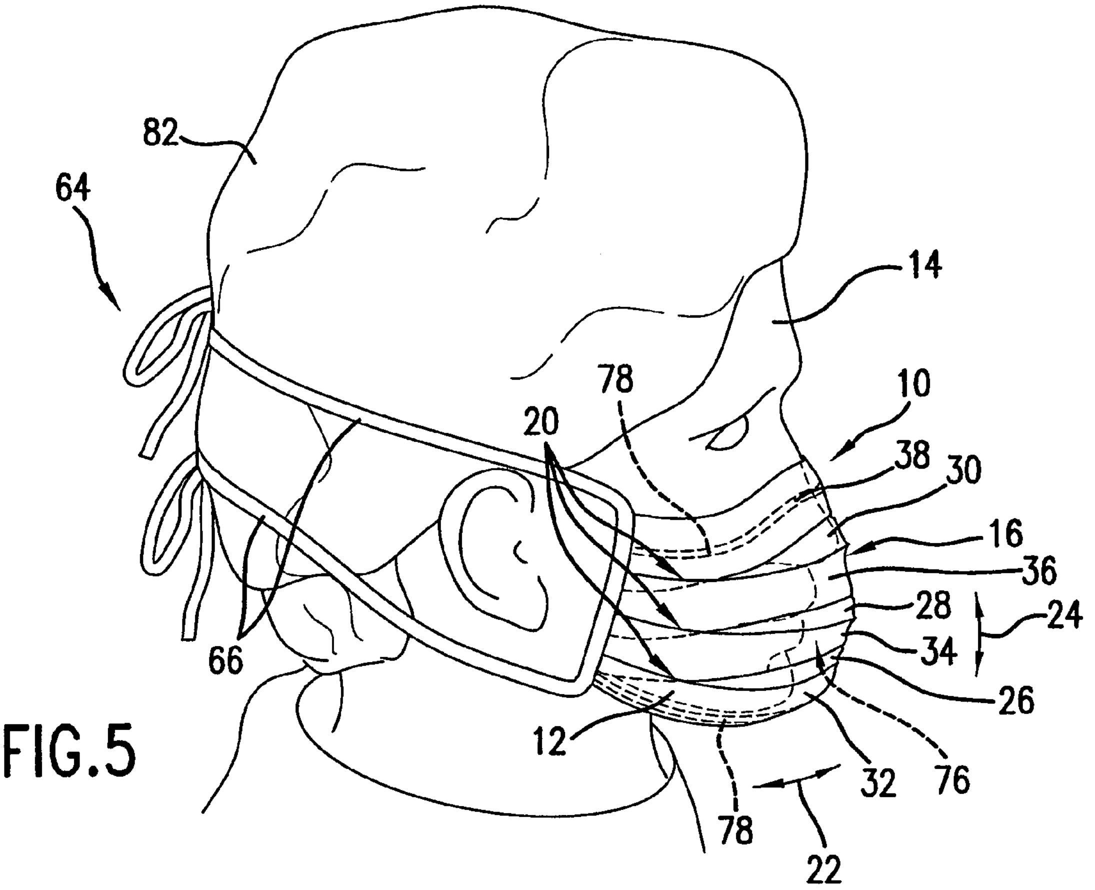
FIG. 5 is a perspective view of an exemplary embodiment of a face mask shown placed on the face of a user.

Folds 20 can be opened so as to extend the vertical length 24 of the layer 16 and thus allow for adjustment of the size or shape of the face mask 10. FIG. 5 shows an exemplary embodiment of the face mask 10 when worn by the user 14. The body portion 12 and the face of the user 14 define a chamber 76. The aforementioned arrangement of folds 20 causes the inner surface 18 of layer 16 to be configured so that air flow within the chamber 76 is directed downward and/or away from eye wear or a face shield that may be worn by the user 14. This redirection reduces the likelihood of undesirable fogging of the eye wear or face shield. The arrangement of the inner surface 18 of layer 16 also assists in redirecting the air flow in chamber 76 so as to be directed into the layer 16 in a direction away from the eye wear and/or face shield of the user 14. As such, the folding pattern of the folds 20 are arranged so as to reduce the likelihood of fogging of eye wear and/or a face shield worn by the user 14.

The body portion 12 of the face mask 10 may be made of inelastic materials. Alternatively, the material used to construct the body portion 12 can be comprised of elastic materials, allowing for the body portion 12 to be stretched over the nose, mouth, and/or face of the user 14. The use of an elastic material incorporated into the body portion 12 allows for fuller coverage of the user's 14 face and provides for more flexibility in accommodating variously sized faces of the users 14. As such, the material that makes up the face mask 10 exhibits elastic or inelastic characteristics depending upon the user's 14 needs.

The body portion 12 of the face mask 10 may be configured so that it is capable of stretching across the face of the user 14 from ear to ear and/or nose to chin. The ability of the body portion 12 to stretch and recover may provide the face mask 10 with better sealing capabilities and a more comfortable fit than face masks 10 that have an inelastic body portion 12. In order for the body portion 12 to stretch and recover, the body portion 12 must have at least one layer or a material that has stretch and recovery properties. Additionally, the entire face mask 10 may be composed of a material that has stretch and recovery properties in other exemplary embodiments of the present invention. In certain exemplary embodiments, the percent recovery is about 15% and the percent stretch is between 15-65%, in other embodiments the percent recovery is between 20-40% stretch, and in still other embodiments the percent recovery is about 25-30% stretch.

Figure 7:
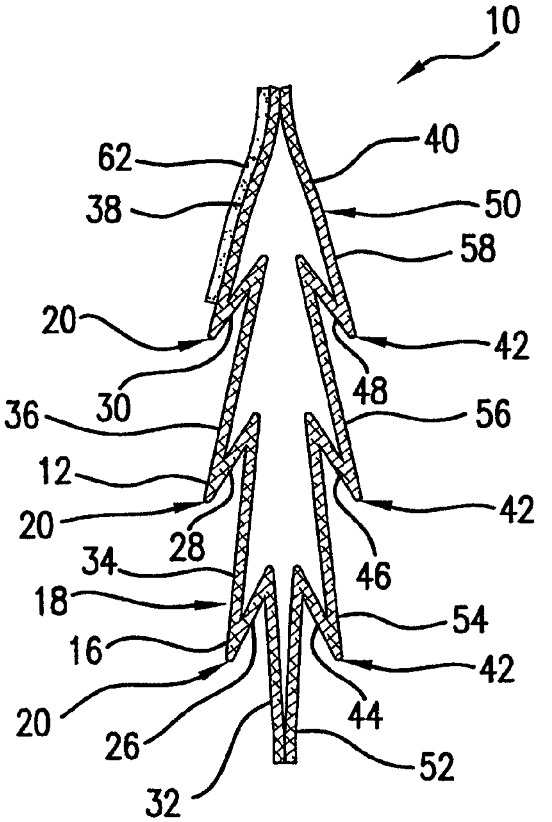
FIG. 7 is a cross-sectional view of an exemplary embodiment of a face mask that has a body portion with a second layer that is folded.

FIG. 7 shows a cross-sectional view of an exemplary embodiment of a body portion 12. Here, a second layer 40 is provided and is configured with the layer 16 so as to form the body portion 12. The second layer 40 has an outer surface 50 that faces towards the environment when the face mask 10 is worn by the user 14 (FIG. 5). The second layer 40 includes a plurality of folds 42 that allow for adjustment of the length and/or shape of the second layer 40. The folds 42 are made from a plurality of fold forming portions 44, 46 and 48 that are intermittent a plurality of primary portions 52, 54, 56 and 58 of the second layer 40. The folds 42 are arranged so that pockets that are formed on the outer surface 50 are eliminated thus reducing the possibility that splashed or dripped fluids may collect on the outer surface 50 and be subsequently transferred through the second layer 40 so as to be inhaled by or contact the user 14.

The fold forming portion 44 is arranged so that the outer surface 50 of the fold forming portion 44 is in facing relationship with the outer surface 50 of the primary portion 52 that is vertically disposed below the fold forming portion 44. Additionally, the outer surface 50 of the fold forming portion 44 is in opposing relationship with the outer surface 50 of the primary portion 54 that is vertically disposed above the fold forming portion 44. The fold forming portions 46 and 48 that form the other folds 42 in the second layer 40 are arranged in a similar manner so that pockets on the outer surface 50 are eliminated. In this regard, the outer surface 50 of the fold forming portion 46 is arranged so as to be in facing relationship with the outer surface 50 of the primary portion 54 that is vertically disposed below the fold forming portion 48. The outer surface 50 of the fold forming portion 46 is in opposing relationship with the outer surface 50 of the vertically disposed upper primary portion 56. Likewise, the outer surface 50 of the fold forming portion 48 is in facing relationship with the outer surface 50 of the vertically disposed lower primary portion 56, and the outer surface 50 of the fold forming portion 48 is in opposing relationship with the outer surface 50 of the vertically disposed upper primary portion 58.

Although all of the folds 42 of the second layer 40 are shown as being arranged in a similar fashion in FIG. 7, it is to be understood that various ones of the folds 42 may be arranged in different manners in accordance with various exemplary embodiments. Additionally, it is to be understood that in accordance with other exemplary embodiments that the second layer 40 with the arrangement of the folds 42 need not be present.

Figure 8:
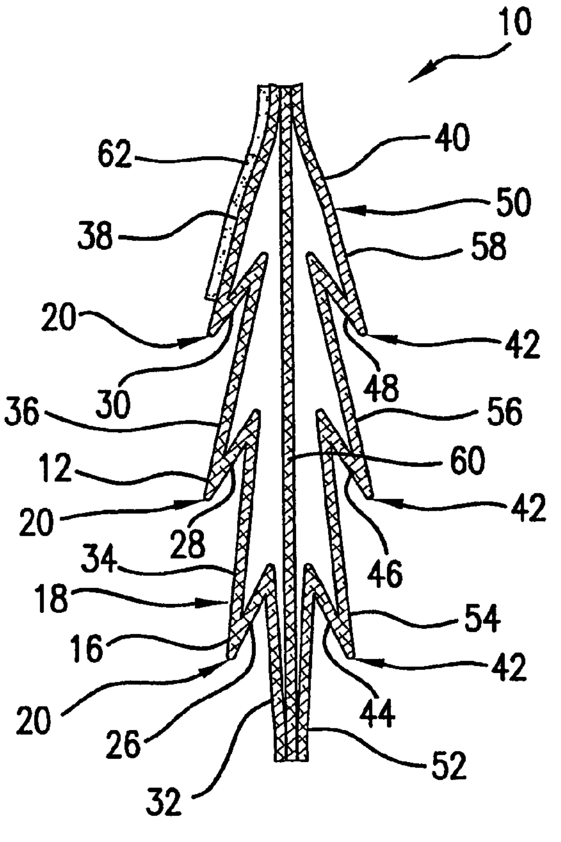
FIG. 8 is a cross-sectional view of an exemplary embodiment of a face mask that has a body portion with a second layer that is folded and a third layer that is unfolded.

FIG. 8 shows an exemplary embodiment in which a third layer 60 is disposed between the layer 16 and the second layer 40. The third layer 60 is not folded and is made of an elastic material to allow layers 16 and 40 to unfold. The third layer 60 is sized so as to extend across the entire horizontal length 22 (FIG. 3) of the layer 16 and to extend across the entire vertical length 24 (FIG. 3) of the layer 16. Alternatively, the third layer 60 can be configured in other exemplary embodiments so as to extend across only a portion of, or so as to extend across more than, the horizontal length 22 and/or the vertical length 24 of the layer 16. Likewise, the second layer 40 extends across only a portion of the horizontal length 22 and/or the vertical length 24 of the layer 16, or the second layer 40 extends across more than the horizontal length 22 and/or the vertical length 24 of the layer 16 in accordance with various exemplary embodiments. Multiple layers of the face mask 10 may be joined by various methods, including adhesive bonding, thermal point bonding, or ultrasonic bonding.

In accordance with one exemplary embodiment three layers 16, 40 and 60 are included in the body portion 12. The layer 16 is a wet laid material that is ½ polyester and ½ pulp. The second layer 40 is a spunbond material, and the third layer 60 is a meltblown material in accordance with one exemplary embodiment.

The third layer 60 is a filtration media configured to prevent the passage of pathogens through the body portion 12 while still allowing for the passage of air in order to permit the user 14 (FIG. 5) to breath. As can be imagined, the layers 16, 40 and 60 are configured so that any of the layers 16, 40 and 60 include filtration media. For instance, both of the layers 16 and 40 may include filtration media in accordance with one exemplary embodiment. Although shown as having three layers 16, 40 and 60, it is to be understood that in other exemplary embodiments, that the body portion 12 and/or the entire face mask 10 can be made of any number of layers.

Figure 9:
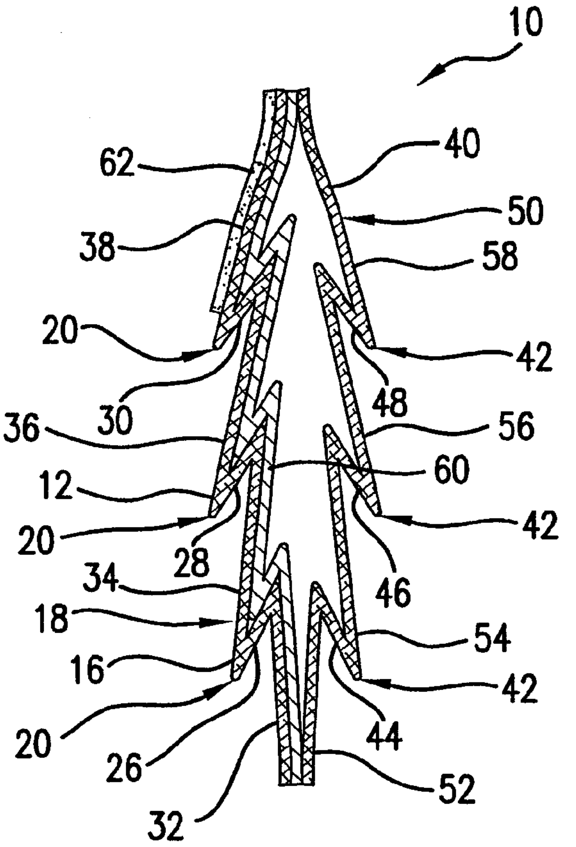
FIG. 9 is a cross-sectional view of an exemplary embodiment of a face mask that has a body portion with a folded second layer and a folded third layer.

FIG. 9 is a cross-sectional view of an exemplary embodiment of the body portion 12 in which the second layer 40 and a third layer 60 are present. The third layer 60 is folded so as to have folds that nest within the folds 20 within the layer 16. The third layer 60 is made of the same material as the layer 16 or is made of a different material than the layer 16. As can be imagined, additional layers may be incorporated into the body portion 12 and are folded or unfolded and configured in any manner commonly known to one having ordinary skill in the art. It is therefore the case that the body portion 12 may include only a single layer 16 or may be multi-layered in accordance with various exemplary embodiments.

Additionally, although the second layer 40 is shown as having folds 42 with a particular folding pattern it is to be understood that the second layer 40 can be configured differently in accordance with various exemplary embodiments. For instance, the folds 42 can be arranged as those in the third layer 60 so as to be nested therewith. Alternatively, the second layer 40 can be unfolded in accordance with various exemplary embodiments.

Figure 10:
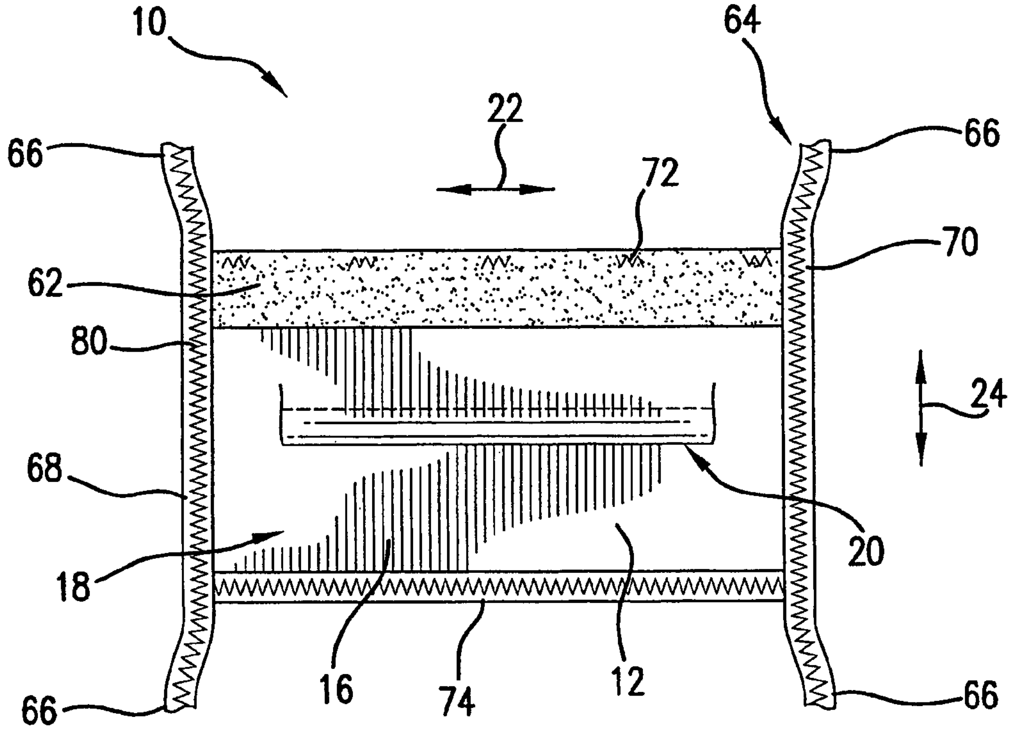
FIG. 10 is a back view of an exemplary embodiment of a face mask that has a body portion with a single fold that extends across only a portion of the length of the body portion.

FIG. 10 shows a further exemplary embodiment of the face mask 10. The body portion 12 has a layer 16 that includes only a single fold 20. The fold 20 extends across only a portion of the horizontal length 22 of the layer 16. The fold 20 is configured as described in the exemplary embodiment shown in FIGS. 3 and 4 so as to help achieve a desired air flow in the face mask 10. It is to be understood, however, that any number of folds 20 may be employed in accordance with various exemplary embodiments. For instance, five, seven, eight or ten folds 20 may be used in accordance with various exemplary embodiments. Further, one or more of the folds 20 can extend across the entire horizontal length 22 of the layer 16 while other folds 20 extend across only a portion of the horizontal length 22 of the layer 16 in accordance with various exemplary embodiments.

Figure 6:
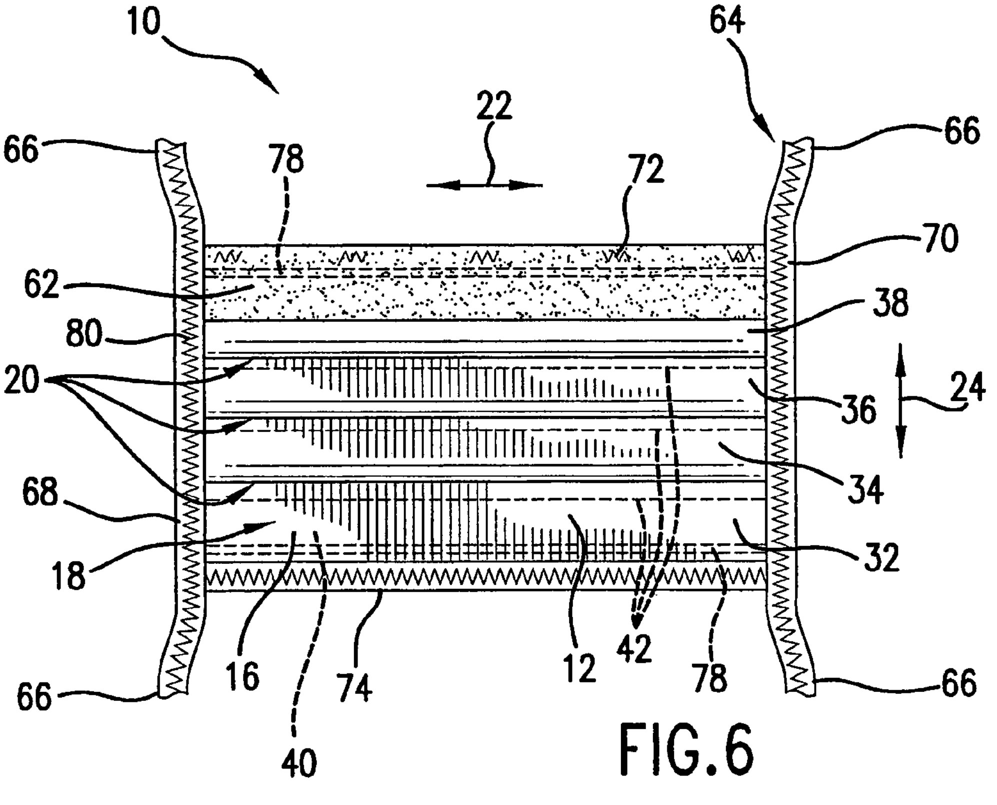
FIG. 6 is a back view of an exemplary embodiment of a face mask. The face mask includes a plurality of folds, stays and an anti-fog strip.

The folds 20 and 42, as shown for instance in the exemplary embodiment of FIG. 6, in the layers 16 and 40 may be of any type commonly known to one having ordinary skill in the art. The side edges of the layers 16 and 40 can be held together by any method commonly known to one having ordinary skill in the art. For instance, ultrasonic bonding, as represented by individual ultrasonic bond dimples 80, can be used in order to hold the layers 16 and 40 together. It is to be understood that other ultrasonic bonding patterns can be employed to facilitate holding of the layers 16 and 40 to one another. FIG. 6 shows bindings 68 and 70 on either side of the body portion 12 used in order to constrain unfolding of the layers 16 and 40. Additionally, binding 72 may be located on the top edge of the body portion 12 and binding 74 may be located on the bottom edge of the body portion 12. The bindings 68, 70, 72 and 74 may be of any type commonly known to one having ordinary skill in the art as previously discussed.

In accordance with another exemplary embodiment, an anti-fog strip 62 is attached to layer 16 and run along the horizontal direction of the body portion 12. The anti-fog strip 62 is attached by way of binding 72 or is attached to the layer 16 in any manner commonly known to one having ordinary skill in the art such as through adhesion or staples. The anti-fog strip 62 assists in redirecting exhaled breath of the user 14 (FIG. 5) into the layers 16 and 40 of the body portion 12 and away from the eyes of the user 14. The anti-fog strip 62 may act to seal the periphery of the upper edge of the body portion 12 so that warm, moist exhaled breath cannot be directed therethrough. The anti-fog strip 62 may be configured as that shown in U.S. Pat. No. 6,520,181 to Baumann, et al., the entire contents of which are incorporated herein by reference in their entirety for all purposes.

It is to be understood, however, that the body portion 12 can be of a variety of styles and geometries, such as, but not limited to, flat half masks, pleated face masks, cone masks, duckbill style masks, trapezoidally shaped masks, etc. The styles shown in the Figures are for illustrative purposes only. The body portion 12 can be configured as that shown in U.S. Pat. No. 6,484,722 to Bostock, et al., the entire contents of which are incorporated by reference herein in their entirety for all purposes. As shown in FIG. 5, the face mask 10 isolates the mouth and the nose of the user 14 from the environment. Additionally, the configuration of the face mask 10 is different in accordance with various exemplary embodiments. In this regard, the face mask 10 is made such that it covers both the eyes, hair, nose, throat, and mouth of the user 14. As such, the present invention includes face masks 10 that cover areas above and beyond simply the nose and mouth of the user 14.

The face mask 10 is attached to the user 14 by a fastening member 64 that is a pair of tie straps 66 that are wrapped around the head of the user 14 (and a hair cap 82 if worn by the user 14) and are connected to one another. It is to be understood, however, that other types of fastening members 64 are employed in accordance with various exemplary embodiments. For instance, instead of the tie straps 66, the face mask 10 can be attached to the user 14 by a fastening member 64 that is ear loops, elastic bands wrapped around the head of the user 14, a hook and loop type fastener arrangement, or a connection directly attaching the face mask 10 to the hair cap 82.

The exemplary embodiment shown in FIG. 6 includes a series of structural elements (stays) 78 incorporated into the body portion 12 in order to provide for a face mask 10 with different desired characteristics. The stays 78 provide for structural rigidity of the body portion 12 and are also shaped in order to help seal the periphery of the body portion 12. Alternatively, a stay 78 is employed within the body portion 12 in order to help conform the body portion 12 around the nose of the user 14 (FIG. 5).

Additionally, a stay 78 is employed in order to better shape the body portion 12 around the chin of the user 14 (FIG. 5). The stays 78 allow for a better fit of the body portion 12 and are used to help form a chamber 76 around the mouth and/or nose of the user 14. The stays 78 help achieve a better fit so as to prevent the transfer of pathogens through any possible openings along the perimeter of the body portion 12. A series of stays 78 incorporated into a face mask 10 is disclosed in U.S. Pat. No. 5,699,791, to Sukiennik et al., the entire contents of which are incorporated herein by reference in their entirety for all purposes. Stays 78 are made of an elongated malleable member such as a metal wire or an aluminum band that can be formed into a rigid shape in order to impart this shape into the body portion 12 of the face mask 10. Of course, various exemplary embodiments exist that do not include stays 78.

The face mask 10 may also incorporate any combination of known face mask 10 features, such as visors or shields, anti-fog strips 62, sealing films, beard covers, etc. Exemplary faces masks and features incorporated into face masks are described and shown, for example, in the following U.S. Pat. Nos. 4,802,473; 4,969,457; 5,322,061; 5,383,450; 5,553,608; 5,020,533; and 5,813,398. The entire contents of these patents are incorporated by reference herein in their entirety for all purposes.

As stated, the mask face 10 may be composed of layers 16, 40 and 60 as shown for instance in FIG. 8. These layers 16, 40 and 60 are constructed from various materials known to those skilled in the art. For instance, the second layer 40 of the body portion 12 may be any nonwoven web, such as a spunbonded, meltblown, or coform nonwoven web, a bonded carded web, or a wetlaid composite. The second layer 40 of the body portion 12 and layer 16 may be a necked nonwoven web or a reversibly necked nonwoven web. The layers 16, 40 and 60 can be made of the same material or of different materials.

Many polyolefins are available for nonwoven web production, for example polyethylenes such as Dow Chemical's ASPUN® 6811A linear polyethylene, 2553 LLDPE and 25355, and 12350 polyethylene are such suitable polymers. Fiber forming polypropylenes include, for example, Exxon Chemical Company's Escorene® PD 3445 polypropylene and Himont Chemical Co.'s PF-304. Many other suitable polyolefins are commercially available as are known to those having ordinary skill in the art.

The various materials used in construction of the face mask 10 may include a necked nonwoven web, a reversibly necked nonwoven material, a neck bonded laminate, and elastic materials such as an elastic coform material, an elastic meltblown nonwoven web, a plurality of elastic filaments, an elastic film, or a combination thereof. Such elastic materials have been incorporated into composites, for example, in U.S. Pat. No. 5,681,645 to Strack et al., U.S. Pat. No. 5,493,753 to Levy et al., U.S. Pat. No. 4,100,324 to Anderson et al., and in U.S. Pat. No. 5,540,976 to Shawver et al, the entire contents of these patents are incorporated herein by reference in their entirety for all purposes. In an exemplary embodiment where an elastic film is used on or in the body portion 12, the film must be sufficiently perforated to ensure that the user 14 (FIG. 5) can breathe through the body portion 12 if the face mask 10 is desired to be breathable in this location.

The third layer 60 when configured as a filtration layer may be a meltblown nonwoven web and, in some embodiments, may be an electret. Electret treatment results in a charge being applied to the third layer 60 that further increases filtration efficiency by drawing particles to be filtered toward the third layer 60 by virtue of their electrical charge. Electret treatment can be carried out by a number of different techniques. One technique is described in U.S. Pat. No. 5,401,446 to Tsai et al., the entire contents of which are incorporated herein by reference in their entirety for all purposes. Other methods of electret treatment are known in the art, such as that described in U.S. Pat. No. 4,215,682 to Kubik et al.; U.S. Pat. No. 4,375,718 to Wadsworth; U.S. Pat. No. 4,592,815 to Nakao and U.S. Pat. No. 4,874,659 to Ando, the entire contents of these patents are incorporated herein by reference in their entirety for all purposes.

The third layer 60 may be made of an expanded polytetrafluoroethylene (PTFE) membrane, such as those manufactured by W. L. Gore & Associates. A more complete description of the construction and operation of such materials can be found in U.S. Pat. Nos. 3,953,566 and 4,187,390 to Gore, the entire contents of these patents are incorporated herein by reference in their entirety for all purposes. The expanded polytetrafluoroethylene membrane can be incorporated into a multi-layer composite, including, but not limited to, an outer nonwoven web second layer 40, an extensible and retractable layer, and an inner layer 16 comprising a nonwoven web.

As stated, any material or materials may be used in the face mask 10. For instance, SMS may be used to comprise the layers 16, 40 and 60. SMS is a meltblown layer made of meltblown fibers between two spunbond layers made of spunbond fibers. Any one of or all of the layers 16, 40 and 60 may be made of a medical grade material so as to prevent pathogens from traveling therethrough.

Elastomeric thermoplastic polymers may be used in the face mask 10 and may include block copolymers having the general formula A-B-A' or A-B, where A and A' are each a thermoplastic polymer endblock which contains a styrenic moiety such as a poly (vinyl arene) and where B is an elastomeric polymer midblock such as a conjugated diene or a lower alkene polymer. Block copolymers of the A-B-A' type can have different or the same thermoplastic block polymers for the A and A' blocks, and the present block copolymers are intended to embrace linear, branched and radial block copolymers. Examples of useful elastomeric resins include those made from block copolymers such as polyurethanes, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene) and the like.

One or more layers 16, 40 and 60 of the face mask 10 may be made of a composite that is a neck bonded laminate in certain exemplary embodiments. The neck bonded laminate may utilize a necked material or a reversibly necked material. The necking process typically involves unwinding a material from a supply roll and passing it through a brake nip roll assembly at a given linear speed. A take-up roll or nip, operating at a linear speed greater than that of the brake nip roll, draws the material and generates the tension needed to elongate and neck the fabric. When a reversibly necked material is desired, the stretched material is heated and cooled while in a stretched condition. The heating and cooling of the stretched material causes additional crystallization of the polymer and imparts a heat set. The necked material or reversibly necked material is then bonded to an elastic material. Afterwards, the layer may be folded in order to form folds 20 and 42 (FIG. 3). The resulting necked composite is extensible and retractable in the cross-machine direction, that is the direction perpendicular to the direction the material is moving when it is produced. Upon extension and release, the elastic material provides the force needed for the extended composite to retract.

In another exemplary embodiment, the composite making up one or more of the layers 16, 40 and 60 may be a stretch bonded laminate. A stretch bonded laminate is formed by providing an elastic material, such as a nonwoven web, filaments, or film, extending the elastic material, attaching it to a gatherable material, and releasing the resulting laminate. A stretch bonded laminate is extensible and retractable in the machine direction, that is the direction that the material is moving when it is produced. A composite with multiple layers may be formed by providing the elastic layer and the gatherable layers, and subjecting it to this process either simultaneously or stepwise. The stretch bonded laminate may also include a necked material that is extensible and retractable in the cross-direction such that the overall laminate is extensible and retractable in at least two dimensions. As an illustration, to construct a two-layer composite that is extensible and retractable in at least two dimensions, an elastomeric meltblown nonwoven web is provided, the elastomeric meltblown nonwoven web is then extended in the machine direction, and the necked spunbonded nonwoven material is attached to the elastomeric meltblown nonwoven web by thermal bonding while the elastomeric meltblown web is extended. When the biasing force is released, the resulting composite is extensible and retractable in both the cross-direction and machine direction, due to the extensibility of the necked material and the use of the stretch bonding process, respectively. The composite may then be folded in order to form folds 20 and 42 (FIG. 3) and attached to or otherwise incorporated with one or more layers to make up the body portion 12.

Additional examples of processes to make such composites are described in, but not limited to, U.S. Pat. No. 5,681,645 to Strack et al., U.S. Pat. No. 5,492,753 to Levy et al., U.S. Pat. No. 4,100,324 to Anderson et al., and in U.S. Pat. No. 5,540,976 to Shawver et al., the entire contents of these patents are incorporated herein by reference in their entirety for all purposes.

The composite may contain various chemical additives or topical chemical treatments in or on one or more layers, including, but not limited to, surfactants, colorants, antistatic chemicals, antifogging chemicals, fluorochemical blood or alcohol repellents, lubricants, or antimicrobial treatments.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

SAMPLE TEST CARRIED OUT IN ACCORDANCE WITH ONE EXEMPLARY EMBODIMENT

A face mask 10 that included a layer 16 with folds 20 arranged in a manner similar to the folds 20 shown in FIGS. 3 and 4 was attached to a head of a mannequin. The mannequin was capable of exhaling warm moist air in order to simulate human respiration. Glasses were placed on the mannequin and the fogging performance of the face mask 10 was evaluated. The face mask 10 prevented fogging from occurring on the eye wear worn by the mannequin.

What is claimed:

1. A face mask, comprising:

a body portion configured to be placed over a mouth and at least part of a nose of a user in order to isolate the mouth and the at least part of the nose of the user from the environment such that respiration air is directed through said body portion;

said body portion has a layer with an inner surface a part of which is configured for contacting the face of the user, said layer has a plurality of folds that extend across the entire horizontal length of said layer;

each of said folds has a fold forming portion located between and attached to two primary portions of said layer, said inner surface of said fold forming portion is in facing relationship with said inner surface of the vertically disposed lower said primary portion;

said inner surface of said fold forming portion is in opposing relationship with said inner surface of the vertically disposed upper said primary portion; and an anti-fog strip located on said inner surface of said body portion along a top edge of said body portion so as to seal against the user's face.

2. The face mask as set forth in claim 1, wherein said body portion has a second layer with an outer surface at least a part of which is configured for facing the environment, said second layer having a plurality of folds that extend across the entire horizontal length of said second layer, wherein each of said folds in said second layer has a fold forming portion located between and attached to two primary portions of said second layer, wherein said outer surface of said fold forming portion of said second layer is in facing relationship with said outer surface of the vertically disposed lower said primary portion of said second layer, and wherein said outer surface of said fold forming portion of said second layer is in opposing relationship with said outer surface of the vertically disposed upper said primary portion of said second layer.

3. The face mask as set forth in claim 2, wherein said body portion has a third layer disposed between said layer and said second layer.

4. The face mask as set forth in claim 3, wherein said layer is made of a wet laid material, wherein said second layer is made of a spunbond material, and wherein said third layer is made of a meltblown material.

5. The face mask as set forth in claim 1, further comprising a fastening member attached to said body portion and configured for attaching said body portion onto the face of the user and sealing the periphery of said body portion to the face of the user.

6. The face mask as set forth in claim 5, wherein said fastening member is a pair of manual tie straps.

7. The face mask as set forth in claim 1, wherein said body portion has binding on a pair of horizontal ends of said body portion so as to limit unfolding of said plurality of folds.

8. The face mask as set forth in claim 1, wherein said plurality of folds are configured to be at least partially unfolded so as to shape said body portion such that said inner surface at least partially defines a chamber when said body portion is placed over the mouth and at least part of the nose of the user.

9. The face mask as set forth in claim 1, wherein said layer is made of a medical grade material.

10. A face mask, comprising:

a body portion that has a layer with an inner surface configured for facing the face of a user, said layer having at least one fold that extends in a horizontal direction across at least a portion of said layer, wherein said fold has a fold forming portion located between and attached to two primary portions of said layer, and wherein said inner surface of said fold forming portion is in facing relationship with said inner surface of the vertically disposed lower said primary portion; and further comprising an anti-fog strip located on said inner surface of said body portion layer along a top edge of said body portion so as to seal against the user's face.

11. The face mask as set forth in claim 10, wherein said inner surface of said fold forming portion is in opposing relationship with said inner surface of the vertically disposed upper said primary portion.

12. The face mask as set forth in claim 10, wherein said fold extends across the entire horizontal length of said layer.

13. The face mask as set forth in claim 10, wherein said body portion has a second layer with an outer surface at least a part of which is configured for facing the environment, said second layer having a plurality of folds that extend along at least a portion of the horizontal length of said second layer, wherein each of said folds in said second layer has a fold forming portion located between and attached to two primary portions of said second layer, wherein said outer surface of said fold forming portion of said second layer is in facing relationship with said outer surface of the vertically disposed lower said primary portion of said second layer.

14. The face mask as set forth in claim 13, wherein said outer surface of said fold forming portion of said second layer is in opposing relationship with said outer surface of the vertically disposed upper said primary portion of said second layer.

15. The face mask as set forth in claim 13, wherein said body portion has a third layer made of a meltblown material disposed between said layer and said second layer, and wherein said layer is made of a wet laid material, and wherein said second layer is made of a spunbond material.

16. The face mask as set forth in claim 10, further comprising a fastening member attached to said body portion and configured for attaching said body portion onto the face of the user and sealing the periphery of said body portion to the face of the user.

17. The face mask as set forth in claim 16, wherein said fastening member is a pair of manual tie straps.

18. The face mask as set forth in claim 10, wherein said body portion has binding on a pair of horizontal ends of said body portion so as to limit unfolding of said fold.

19. The face mask as set forth in claim 10, wherein said fold is configured to be at least partially unfolded so as to shape said body portion such that said inner surface at least partially defines a chamber when said body portion is placed over the mouth and at least part of the nose of the user.

20. The face mask as set forth in claim 10, wherein said layer is made of a medical grade material.

* * * * *